US00PP35558P2

(12) United States Plant Patent
Valin

(10) Patent No.: US PP35,558 P2
(45) Date of Patent: Dec. 26, 2023

(54) ***WEIGELA* PLANT NAMED 'TMWG18-02'**

(50) Latin Name: *Weigela florida*
Varietal Denomination: TMWG18-02

(71) Applicant: Branded Garden Products Ltd., Ipswich (GB)

(72) Inventor: Charles Valin, Ipswich (GB)

(73) Assignee: Branded Garden Products Ltd., Ipswich (GB)

( * ) Notice: Subject to any disclaimer, the term of this patent is extended or adjusted under 35 U.S.C. 154(b) by 0 days.

(21) Appl. No.: 18/185,792

(22) Filed: Mar. 17, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Weatherly IP Solutions, LLC; James M. Weatherly

(57) ABSTRACT

A new cultivar of *Weigela* plant named 'TMWG18-02' that is characterized by compact growth habit, very dark, almost black, foliage, and large trumpet-shaped flowers with widely flared mouths. Plants of 'TMWG18-02' which are established before winter bear flowers early and profusely in spring and achieve a height and width of 25 cm. in their first growing season.

2 Drawing Sheets

Genus and species: *Weigela florida.*
Variety denomination: 'TMWG18-02'.

BACKGROUND OF THE NEW PLANT

The present invention relates to a new and distinct cultivar of *Weigela*, grown as an ornamental plant for use in the garden and landscape. The new cultivar is known botanically as *Weigela florida* and will be referred to hereinafter by the cultivar name 'TMWG18-02'.

'TMWG18-02' originated from a *Weigela* breeding program which the inventor carried out at the inventor's nursery in Ipswich, United Kingdom. The inventor had assembled a collection of *Weigela* varieties (both commercial varieties and inventor's proprietary selections). After hand pollination between many of the assembled plants, seeds were collected, sown, grown on and planted in the field for evaluation. The identities of the parents of 'TMWG18-02' are unknown.

The new cultivar 'TMWG18-02' was selected in the field in 2018 for its combination of compact plant habit, very dark foliage and early production of large pink-purple tubular flowers with wide mouths.

The inventor first asexually reproduced 'TMWG18-02' in 2018 in Ipswich, United Kingdom by the method of softwood cuttings. The inventor has determined that the unique characteristics of 'TMWG18-02' are stable and reproduce true to type in successive generations of asexual reproduction.

SUMMARY

The following traits have been repeatedly observed and represent the characteristics of the new *Weigela* cultivar 'TMWG18-02'. 'TMWG18-02' has not been tested under all possible conditions and phenotypic differences may be observed with variations in environmental, climatic and cultural conditions, however, without any variance in genotype.

1. 'TMWG18-02' exhibits a compact growth habit.
2. First year flowering plants of 'TMWG18-02' achieve a height and width of 25 cm.
3. The leaves and stems of 'TMWG18-02' are dark grey-purple, almost black in color.
4. Plants of 'TMWG18-02' which are established before winter bear flowers early and profusely in spring.
5. A one year old plant of 'TMWG18-02' bears approximately 150 pink-purple flowers at any time during its April-June peak of flowering.
6. The flowers of 'TMWG18-02' are large, trumpet-shaped, with a wide open flared mouth.
7. 'TMWG18-02' grows well in moist well-drained soils in full sun to partial shade.
8. 'TMWG18-02' is hardy at least to USDA Zone 5.

BRIEF DESCRIPTION OF THE PHOTOGRAPHS

The accompanying color photograph illustrates the overall appearance of the new *Weigela* variety 'TMWG18-02' showing colors as true as it is reasonably possible to obtain in colored reproductions of this type. Colors in the photographs may differ from the color values cited in the detailed botanical description, which accurately describe the observed colors of 'TMWG18-02'.

Figure 1:
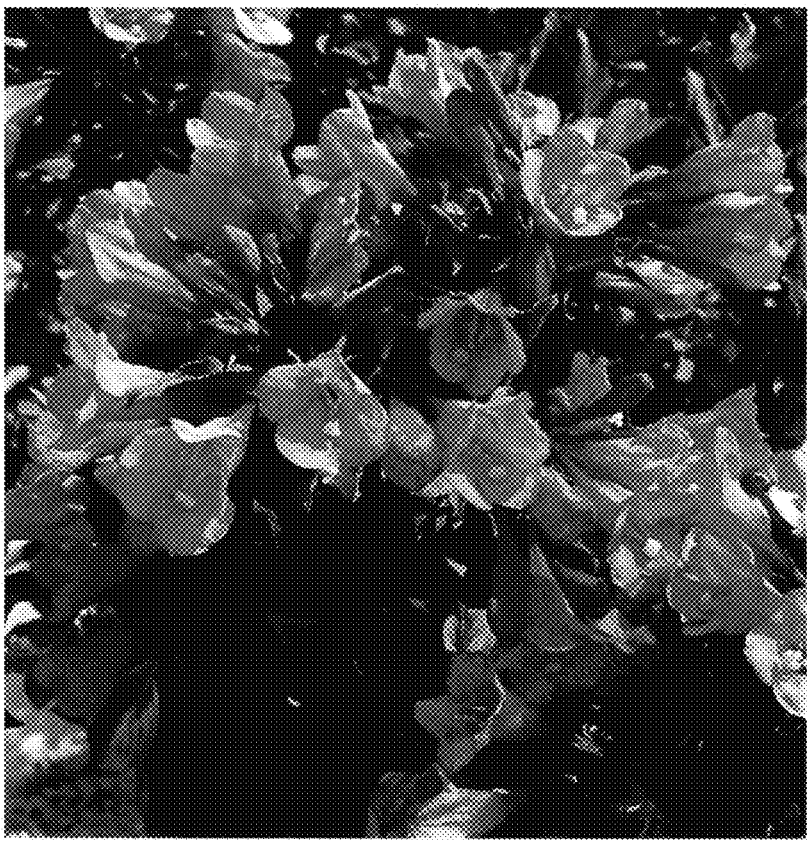

FIG. 1 depicts a whole plant of 'TMWG18-02' in mid-April in full flower in Santa Barbara, California. The illustrated plant is nine months old from planting a rooted cutting into a 13 cm diameter container. The illustrated plant has been grown entirely outdoors in Santa Barbara, California. Except for one pinch or stop at the first leaf node above soil level, the plant has not been pruned further and not been treated with any growth regulating chemicals.

Figure 2:
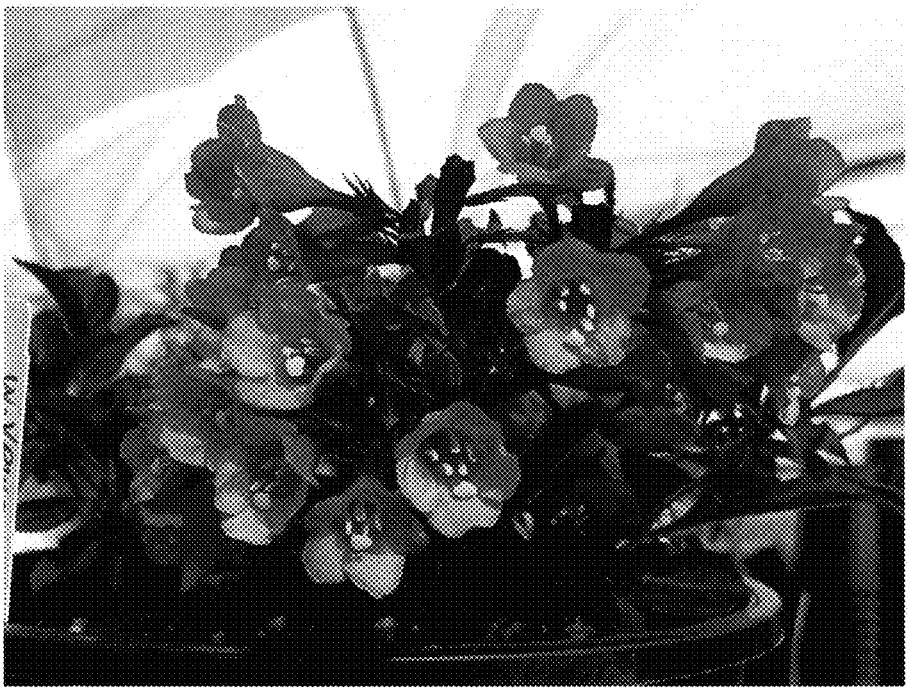

FIG. 2 presents a close-up view of the flowers and buds of 'TMWG18-02' in mid-April.

BOTANICAL DESCRIPTION OF THE PLANT

The following is a detailed description of the new cultivar 'TMWG18-02'. Data was collected in mid-April from nine months old plants in their first season of flower. The plants have been grown entirely outdoors in Santa Barbara, California. Except for one pinch or stop at the first leaf node above soil level, the plant has not been pruned further and not been treated with any growth regulating chemicals. The color determinations are in accordance with the 2007 edition of The Colour Chart of The Royal Horticultural Society, London, England, except where general color terms of ordinary dictionary significance are used.

Botanical classification: *Weigela.*

*Variety.*—'TMWG18-02'.

*Species.—Florida.*

Parentage:

*Female parent.*—Unknown.

*Male parent.*—Unknown.

Plant description:

*Growth habit.*—Compact mound.

*Use.*—In containers and in the landscape.

*Suitable container sizes.*—1 gallon to 3 gallon.

*Dimensions.*—25 cm. in height, 25 cm. in width.

*Hardiness.*—At least hardy to USDA Zone 5.

*Propagation.*—Stem cuttings.

*Time to initiate roots.*—3 to 4 weeks are required to produce roots on an initial cutting.

*Crop time.*—9-10 months to produce a first year flowering plant in a 1 gallon container. Additional years to produce larger specimen plants.

*Root system.*—Fibrous.

*Light.*—Plant in full sun or partial shade.

*Soil.*—Plant in moist but well drained soil.

*Type.*—Deciduous shrub.

*Seasonal interest.*—Extremely floriferous in early-mid spring.

Stem (below first pinch or stop):

*Shape.*—Terete.

*Dimensions.*—5 cm. in length, 1 cm. in diameter at soil level.

*Color.*—N200B.

*Surface.*—Lignified, rough, lenticels present.

*Lenticels.*—Elliptic, length 1.5 mm., width 1.0 mm., slightly raised, color 202B.

Branches:

*Quantity (average).*—5 primary branches and 4 lateral branches per primary branch.

*Primary branch stem dimensions.*—20 cm.-25 cm. in length, 6 mm. in diameter.

*Secondary branch stem dimensions.*—15 cm.-18 cm. in length, 3 mm.-5 mm. in diameter.

*Shape.*—Terete.

*Internode length.*—2.5 cm.-3.5 cm.

*Color.*—Ranges between N186C and N186A.

*Surface.*—Smooth.

Foliage:

*Leaf arrangement.*—Opposite.

*Leaf division.*—Simple.

*Leaf shape.*—Ovate, longitudinally inwardly curved.

*Leaf attachment.*—Very short petiolate.

*Petiole shape.*—Sulcate, adaxial surface concave.

*Petiole dimensions.*—2 mm. to 3 mm. in length and 2.5 mm. in diameter.

*Petiole color.*—N186C.

*Leaf dimensions.*—45 mm.-50 mm. in length, 21 mm.-24 mm. in width.

*Leaf surface (both surfaces).*—Glabrous.

*Leaf color (adaxial surface).*—N187A-N186A.

*Leaf color (abaxial surface).*—N187A except N144D towards base.

*Leaf apex.*—Acute.

*Leaf base.*—Cuneate.

*Leaf margin.*—Finely serrate, glabrous.

*Leaf venation pattern.*—Pinnate.

*Veins (adaxial surface).*—192C.

*Veins (abaxial surface).*—Slightly raised, N144D, midrib puberulent.

Inflorescence, flowers:

*Inflorescence form.*—Each primary and secondary branch bear cymose inflorescences in the terminal leaf axils.

*Flowers.*—Arrangement: Opposite pairs arranged in three whorls. Quantity: Approximately 150 flowers at peak flowering (6 flowers per inflorescence, 25 inflorescences per plant). Aspect: Upward, horizontal and downward facing. Dimensions: Length, including corolla tube: 45 mm.-50 mm. Diameter (fully developed, at flower tube apex): 25 mm-30 mm.

*Bud.*—Shape: Club-shaped, apex capitate with 5 ridges below (fused sepal junctions). Color: 51A. Dimensions: 40 mm. in length, 10 mm. in maximum diameter immediately prior to opening. Surface: Glabrous, minutely glandular.

*Bracteoles.*—Arrangement: Borne in unequal pairs the base of peduncle. Shape: Narrowly lanceolate Dimensions: 3 mm.-6 mm. in length, 1 mm.-1.5 mm. in width. Color (both surfaces): N187A. Surface: Glabrous.

*Peduncle.*—Shape: Terete. Dimensions: 10 mm.-12 mm. in length, 1.5 mm. in diameter. Color: Ranges between N187A and 202A. Surface: Smooth, glabrous.

*Calyx, sepals.*—Calyx shape: Funnel-shaped. Calyx diameter (across sepal apices): 4 mm. (bud calyx), 6 mm. (flower calyx). Sepals: 5 in number, longitudinally fused for approximately half sepal length. Sepal shape: Narrowly lanceolate. Sepal dimensions: 8 mm. to 11 mm. in length, 2 mm. in width. Sepal color (both surfaces): N186A-N186C. Sepal surface (both surfaces): Puberulent.

*Corolla (consists of corolla tube and fused petals to base of free petal lobes).*—Shape: Salverform. Dimensions: 30 mm. in length, 2 mm. in diameter at base, 15 mm. in diameter at base of petal lobes. Surface: Glabrous. Tube color: Adaxial surface: Tube base N186C, tube becoming lighter 51A towards and below the free petal lobes. Abaxial surface: 51A.

*Petals (free petal lobes).*—Number: 5, fused at base. Petal lobe shape: Orbicular. Color (adaxial surface): 62B-62C becoming paler 62D, almost white N155B, when flower is fully expanded. Color (abaxial surface): 62B-62C. Surface texture: Glabrous.

Reproductive organs:

*Number of stamens.*—5, individually fused to corolla tube for most of length.

*Filaments.*—15 mm. in length of which basal 10 mm. fused to corolla tube and 5 mm. free; diameter 0.75 mm. to 1.0 mm. in diameter.

*Filament color.*—51B.

*Anther shape.*—Sulcate.

*Anther dimensions.*—5 mm. in length, 1.5 mm. in width.

*Anther color.*—161D.

*Pollen amount.*—Moderate.

*Pollen color.*—155A.

*Number of pistils.*—1.

*Style.*—35 mm. in length and 1 mm. in diameter.

*Style color.*—51B.

*Style surface.*—Glabrous.

*Stigma shape.*—Capitate, tending to globular.

*Stigma dimensions.*—4 mm. in diameter and 2 mm. in height.

*Stigma color.*—155A with faint ring 70C around abaxial attachment to style.

*Ovary.*—Not observed.

Seed: None observed, pollination has not occurred.

Susceptibility or Resistance to Pests and Diseases: None.

COMPARISON WITH PARENT VARIETIES

The parents of 'TMWG18-02' are unknown. No comparison is available.

COMPARISON WITH CLOSEST KNOWN VARIETY

'TMWG18-02' may be compared with *Weigela* plant named 'Dark Horse' (U.S. Plant Pat. No. 14,381). Whereas both varieties, 'TMWG18-02' and 'Dark Horse' are similarly compact in habit and bear dark foliage and are early to flower, the foliage of 'TMWG18-02' is saturated dark grey-purple almost black in color, whereas the foliage color of 'Dark Horse' lighter grey-purple and tends towards dark olive green rather than black. In addition, the tubular flowers of 'TMWG18-02' develop a wider flared apex than then flowers of 'Dark Horse'.

I claim:

1. A new and distinct cultivar of *Weigela* plant named 'TMWG18-02' as described and illustrated herein.

* * * * *